US 6,539,323 B2

(12) United States Patent
Olson

(10) Patent No.: US 6,539,323 B2
(45) Date of Patent: Mar. 25, 2003

(54) METHODS AND APPARATUS FOR CORRECTING SPECTRAL COLOR MEASUREMENTS

(75) Inventor: Thor A. Olson, Minnetonka, MN (US)

(73) Assignee: Electronics For Imaging, Inc., Foster City, CA (US)

(*) Notice: Subject to any disclaimer, the term of this patent is extended or adjusted under 35 U.S.C. 154(b) by 41 days.

(21) Appl. No.: 09/849,282

(22) Filed: May 4, 2001

(65) Prior Publication Data

US 2002/0165684 A1 Nov. 7, 2002

(51) Int. Cl.⁷ .............................. G01N 21/25
(52) U.S. Cl. .................. 702/104; 702/85; 356/402; 356/408
(58) Field of Search .............. 702/104, 85; 356/402, 356/408, 407, 425, 73, 325, 328, 319; 382/191, 167; 250/226, 559.01

(56) References Cited

U.S. PATENT DOCUMENTS

| | | |
|---|---|---|
| 5,272,518 A | 12/1993 | Vincent |
| 5,673,336 A * | 9/1997 | Edgar et al. ............. 382/167 |
| 5,880,738 A | 3/1999 | Donelly |
| 5,963,333 A | 10/1999 | Walowit |
| 6,020,583 A | 2/2000 | Walowit |
| 6,052,334 A * | 4/2000 | Brumley et al. ........... 367/90 |
| 6,058,357 A | 5/2000 | Granger |
| 6,088,117 A | 7/2000 | Imura |

* cited by examiner

*Primary Examiner*—John Barlow
*Assistant Examiner*—Hien Vo
(74) *Attorney, Agent, or Firm*—Barry R. Lipsitz; Douglas M. McAllister

(57) ABSTRACT

The invention provides methods and apparatus for correcting spectral measurements, such as are obtained by a spectrophotometer for measuring color. A single matrix is used that operates on a raw measurement vector (spectrum) to obtain a corrected spectrum. The matrix may embody a transform that minimizes the difference between the corrected spectra and a set of reference spectra. The difference may be characterized by a set of basis function weighting vectors which are then used to build the correction matrix. Correction of high resolution spectra (very long measurement vectors) is thereby allowed, without the large number of measurements that would normally be required. The reference spectra can be calibration data, or measurements made by another instrument which is desired to be simulated.

22 Claims, 9 Drawing Sheets

METHODS AND APPARATUS FOR CORRECTING SPECTRAL COLOR MEASUREMENTS

BACKGROUND OF THE INVENTION

The present invention relates generally to the measurement of color, and more particularly to the correction of spectral measurements, such as are obtained by a spectrophotometer for measuring color.

Accurate and reliable measurement of color is difficult to achieve, but is essential for successful color reproduction and control. "Color" is the human visual system's response to a specific distribution of light energy in what is termed the "visible spectrum", a portion of the full electromagnetic energy spectrum where the wavelength ranges from 400 nanometers (1 nm =$10^{-9}$ meters) to 700 nm. A plot of light energy versus wavelength is called a spectrum. As an example, a spectrum for the color Magenta is shown in FIG. 1. The various possible shapes of the spectrum plot gives rise to the perception of different colors. For example, spectra which have larger energy amplitudes in the short wavelengths near 400 nm are perceived as being "blue" while spectral plots that show larger amplitudes in the longer wavelengths near 700 nm are perceived as being "red". The set of all possible shapes for a spectral energy plot gives rise to the enormous number of colors that humans can see (nearly 10 million). In the case of visible light, each spectral band of color may be as small as 2 nm wide spanning the range from 400 nm to 700 nm.

A wide variety of instruments are used to make quantitative measurements of color. In general, these instruments can be classified as making either "three-band", or "full spectrum" measurements. The three-band instruments measure the light energy reflected from a sample at three positions within the spectrum. They are not able to detect the entire spectrum of a color, but having a 3-channel estimate of it is very useful for many printing and color control applications, and the expense of making this kind of measurement is low.

Full spectrum instruments are able to obtain the spectral energy distribution of a color across the entire visible spectrum, and thereby gain a more accurate representation of the color characteristics of a sample. For example, such a measurement can be used to predict a sample's color appearance even when the lighting on the sample changes.

The more accurately a spectrum is measured, the better will be the color representation, and so very high resolution spectra (many sampling positions along the wavelength axis) are desirable. It is difficult however, to make accurate and high resolution full spectrum measurements.

For a variety of reasons related to the specific design of an instrument, the amplitude at one position (one wavelength) along the spectrum is influenced by the amplitudes at other wavelengths. This is called "cross-spectrum contamination" or "crosstalk". If the amplitude measured at some position in the spectrum is distorted by crosstalk, the spectrum will misrepresent the color of the sample.

FIG. 2 illustrates an example of this effect. FIG. 2 shows a spectrum of a blue sample. The plot of actual spectra 10 shows that the reflected energy from the sample is highest in the short wavelength region and the spectrum makes a transition to a low level for the rest of the wavelengths. A plot of a spectrum that might be measured by an instrument suffering from spectral crosstalk is shown at 12. Plot 12 shows a rise in energy at the long wavelength end that does not really exist, it is a false measurement of the blue energy showing up as an apparent amount of red. In other words, plot 12 shows energy from the blue end of the spectrum being falsely detected as energy from the red end of the spectrum. The color represented by the measurement will have a reddish tint compared to the actual color.

If it could be determined just how much the blue wavelength energy was influencing the red wavelength measurements, we could compensate for this effect. Unfortunately, a single measurement isn't enough to discover exactly what wavelength is causing the contamination. The contamination could be any of the wavelengths in the blue region, it could be a little contamination from all of the wavelengths, the contamination could be from just a portion of the wavelengths, or from a gradual increase of contamination toward one specific wavelength.

To find out the details of the crosstalk in order to correct for it, many measurements must be taken of unique color spectra, and then the influencing wavelengths must be factored out. The number of measurements that must be made is equal to the number of wavelength positions along the spectrum that are used in the spectral plot. It is common to have at least 30 such positions, but more accurate instruments using higher resolution obtain over 100 individual amplitudes for a spectral plot. It becomes difficult to solve for the crosstalk characteristics for such a large system.

In addition, the nature of the light source used to illuminate a color specimen can have considerable effect on the spectrum that is detected. In particular, the angle of illumination, the texture and gloss of the sample, and the amount of ultraviolet energy in the light and fluorescent material in the sample, all influence the spectrum that is obtained.

Because of these issues, prior art spectral sensing instruments incorporate many different strategies and detection techniques. Any spectral instrument design represents a collection of tradeoffs involving sensitivity, accuracy, specimen size and geometry, cost, power consumption, and the like. These tradeoffs result in considerable variation in instrument designs available on the market, and correspondingly, variations in the color measurements made by them.

It would be advantageous to provide a simple means for correcting spectral color measurements using vectors and matrices. It would be advantageous to provide for the correction of crosstalk effects as well as various other sources of spectral representation error. It would be further advantageous to provide for the correction of spectral color measurements using a single correction matrix. It would be still further advantageous to provide a correction matrix that embodies a transform that minimizes the difference between the corrected spectra and a set of reference spectra. It would be advantageous if the difference between the corrected spectra and the reference spectra could be characterized by a set of basis functions, which can be used to build the correction matrix.

The methods and apparatus of the present invention provide the aforesaid and other advantages.

GENERAL DESCRIPTION OF THE INVENTION

The present invention provides methods and apparatus for correcting spectral measurements, such as are obtained by a spectrophotometer for measuring color. In accordance with the invention, a single matrix operates on a raw measurement vector (spectrum) to obtain a corrected spectrum. The matrix may embody a transform that minimizes the difference between the corrected spectra and a set of reference spectra. The difference may be characterized by a set of basis function weighting vectors which are then used to build the correction matrix. The method allows the correction of high resolution spectra (very long measurement vectors) without requiring the large number of measurements that would normally be required. The reference spectra can be calibration data, or measurements made by another instrument which is desired to be simulated.

This invention provides a way to solve for the crosstalk components without making hundreds of measurements for a high resolution full spectrum color instrument. Instead, a few tens of measurements can be made. The (uncalibrated) color instrument to be characterized is used to obtain spectral measurements of, for example, 24 uniquely colored sample patches. Another instrument, a reference instrument, which is known to be calibrated accurately, also makes measurements and obtains spectra of these same 24 color patches. The spectra from the reference instrument are collected and compared to the set of spectra from the uncalibrated instrument. One spectrum is subtracted from the other to obtain a spectral difference plot or error spectrum for each of the 24 colors.

It would be desirable to compare the error spectra with the original measured spectra to find how they are correlated, but as mentioned previously, it is not possible to uniquely correlate the errors with so few measurements. Such a system is said to be underdetermined, as there are many possible solutions. The number of possible solutions can be reduced, however, by making an approximation to the difference spectra. The approximation requires that each difference spectrum be represented as the sum of a number of (no more than 24 in this example) possible components. These components can be selected so that there is a minimum of residual error in this representation of the difference spectra. Well-established methods of linear algebra are used to find the components for this approximation and are described in detail below.

If the difference spectra can be represented by 24 or fewer components (the number of color patch measurements made), then a unique correlation between the measurement error and the original measured spectrum can be solved for by using standard algebraic methods (also described below). This correlation describes the relationship between the original measurement and any crosstalk error that it might contain. Since this relationship can now be calculated, the error can be computed and subtracted from the original measurement to obtain a new spectrum that no longer contains this crosstalk error.

The concept of correcting a spectral measurement is a common one. A simple correction method is to multiply the spectrum by a scale factor or to subtract an offset. Slightly more sophisticated is to scale the spectrum by a different factor at each wavelength, or to subtract a different offset from the amplitude at each wavelength. All of these operations can be accomplished using matrices, vectors, and a matrix multiply operator. A vector is used to represent the sequence of amplitudes for each wavelength along a spectrum. It is shown as a long rectangle, either horizontally oriented (a row vector), or vertically oriented (a column vector). A matrix is a collection of vectors and forms a larger rectangle. The correction matrix used in the present invention has the same number of rows as columns and may be shown as a square. These elements are combined by the matrix multiplication operation.

The multiple steps of calculating an error spectrum and then subtracting it from the measurement can be combined into a single matrix multiplication operation. The matrix that is used for this one-step procedure is the combination of a crosstalk correlation matrix with an Identity matrix resulting in a correction matrix. The identity matrix serves to represent the original spectrum. Such a technique is possible because of the properties of linear systems.

The correction matrix contains the information that correlates the crosstalk error with the spectral measurement. The actual crosstalk correction amplitudes are obtained by multiplying the spectrum by the matrix. Once the crosstalk correction is obtained, it is added to the spectrum. This is a very general and powerful technique for correcting signals and a number of useful variations are commonly used. The effectiveness of this technique depends critically on the contents of the matrix. The calculation of the correction matrix elements is described in detail below.

In an exemplary embodiment of the invention, spectral measurements of a color sensing device may be corrected. A set of spectral measurements may be obtained by the color sensing device. Each of the spectral measurements represents an amplitude of detected light in a spectral band from a plurality of respective N spectral bands, such that the set of spectral measurements may be represented by a 1×N spectral measurement vector. A set of basis function weighting vectors is calculated based on the difference between measured spectra values for a plurality of color samples and a set of reference spectra values for the same color samples. The calculation of basis function weighting vectors is described in detail below. An N×N transform matrix is formed based on these basis weighting vectors and the measured spectra values. The N×N transform matrix provides mapping between the spectral measurements and corrected spectra. The 1×N spectral measurement vector may be multiplied by the N×N transform matrix to generate a corrected spectrum.

A processor may be provided for multiplying the 1×N spectral measurement vector by the N×N transform matrix to generate the corrected spectrum.

The N×N transform matrix may be obtained by measuring spectra values of a training set of K color samples. Each sample has a known reference reflectance spectra. Once the measured spectra are obtained, the basis function weighting vectors (a representation of the difference between the measured and the reference reflectance spectra) can be solved for using a set of D basis functions. The number of basis functions (D) may be less than or equal to the lesser of K or N. The basis functions may be represented by the D columns in an N×D array, or in any suitable manner. The solution for the basis function weighting vectors may be represented as an array of D×N amplitudes. The N×N matrix can then be formed by adding an identity matrix I to the product of the N×D basis set and the D×N amplitude array.

Basis functions may comprise simple trigonometric functions that are well known and can be specified with a few parameters. Alternately, the basis functions may depend upon characteristics of the differences between the measured spectra values and the reference spectra values. Weightings of the basis functions may be stored in the color sensing device when the basis functions are known and fixed (e.g., when they are a set of simple trigonometric functions). When the basis functions are variable, both the basis functions and associated basis function weightings may be stored in the color sensing device (e.g., when the basis functions are principal components obtained from the measured data).

The known reference reflectance spectra values may be either calibration spectra values or simulation spectra values. The known reference reflectance spectra values may be obtained from a reference instrument.

DETAILED DESCRIPTION OF THE INVENTION

The present invention provides methods and apparatus for calibrating or correcting a spectral color measurement. The calibration may be made with respect to an absolute standard, or may be made with respect to a reference standard. In particular, the present invention provides methods and apparatus for matching a spectral measurement made by a first color sensing device to a spectral measurement made by a second color sensing device (e.g., a reference instrument) without regard to absolute accuracy. The invention corrects for various deficiencies in one instrument or the other such as spectral crosstalk, bandwidth limitations, offsets, and non-uniformities in illumination.

Figure 1:
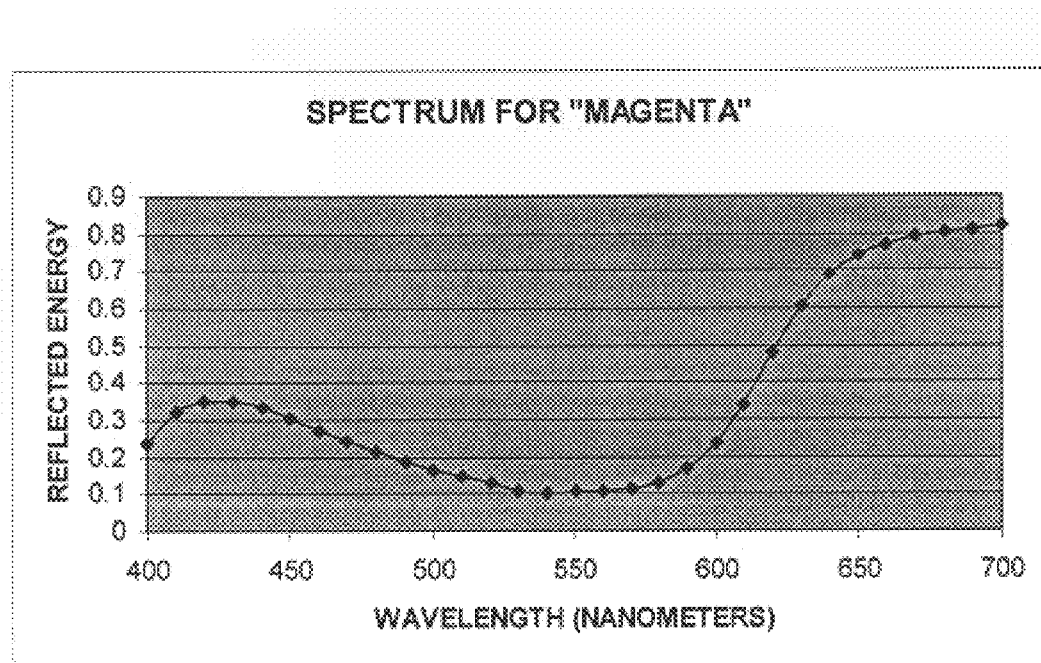
FIG. 1 is an example of a measured spectrum.
Figure 2:
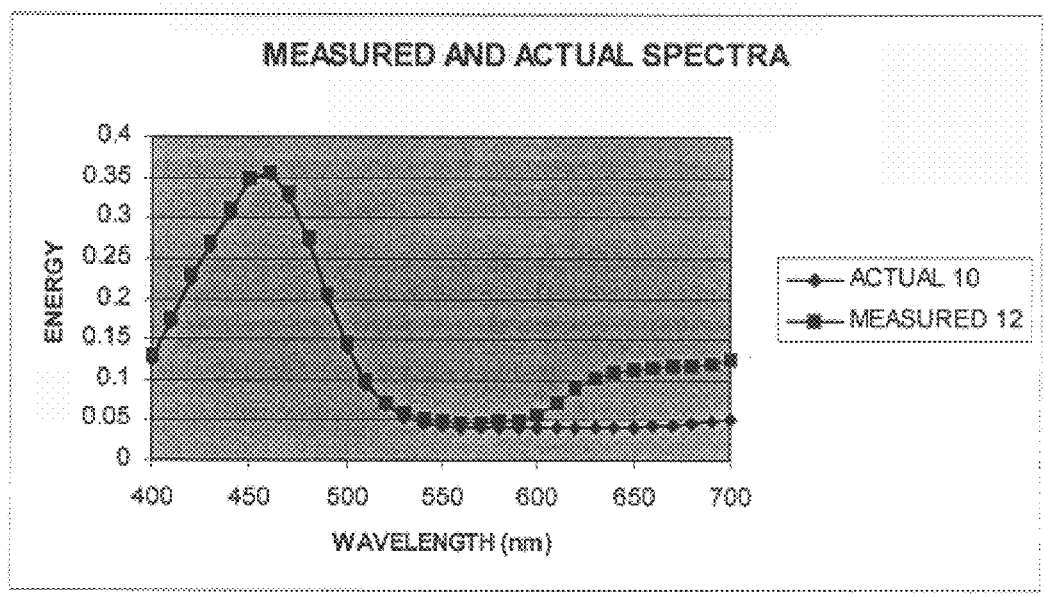
FIG. 2 is an example of an actual spectrum compared with a measured spectrum.
Figure 3:
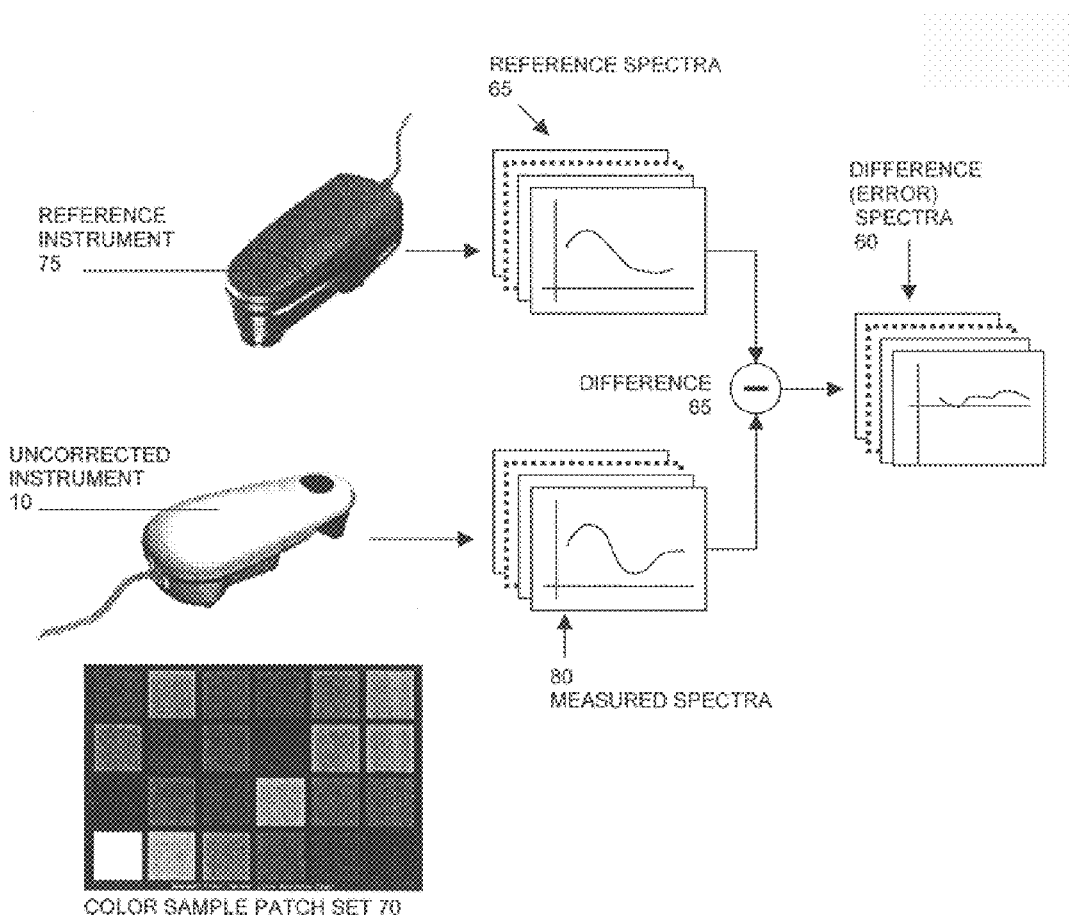
FIG. 3 shows a block diagram of a simplified embodiment of the invention.

This invention provides a way to solve for the crosstalk components without making hundreds of measurements for a high resolution full spectrum color instrument. Instead, a few tens of measurements can be made. A simplified embodiment is shown in FIG. 3. The (uncalibrated) color instrument 10 that is to be characterized, is used to obtain spectral measurements of a training set of color samples, for example, 24 uniquely colored sample patches 70. Another instrument, a reference instrument 75, which is known to be calibrated accurately, also makes measurements and obtains spectra of these same 24 color patches 70. The set of reference spectra 65 from the reference instrument 75 are collected and compare to the set of measured spectra 80 from the uncalibrated instrument 10. One spectrum is subtracted from the other (85) to obtain a spectral difference plot or error spectrum 60 for each of the 24 colors.

It would be desirable to compare the error spectra 60 with the original measured spectra 80 to find how they are correlated. However, it is not possible to uniquely correlate the errors with so few measurements. Such a system is said to be underdetermined, as there are many possible solutions. By making an approximation to the difference spectra, the number of possible solutions can be reduced. This approximation requires that each difference spectrum 60 be represented as the sum of a number of (no more than 24 in this example) possible components. These components can be selected so that there is a minimum of residual error in this representation of the difference spectra 60. Well-established methods of linear algebra are used to find the components for this approximation and are described in detail below.

Figure 4:
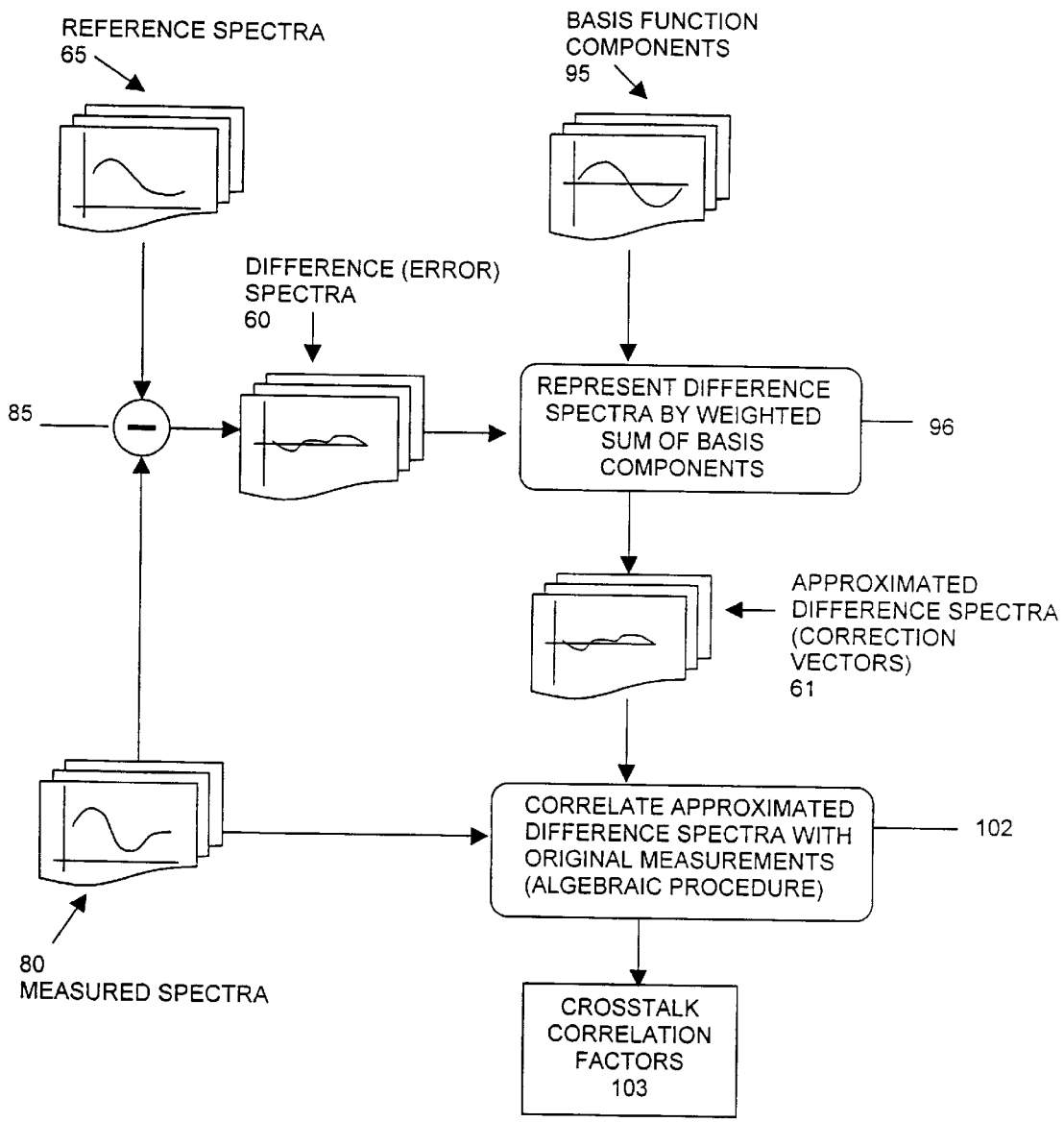
FIG. 4 shows a block diagram of an example of the formation of crosstalk correlation factors from a set of reference spectra.

FIG. 4 shows the formation of crosstalk correlation factors 103 from a set of reference spectra 65. Reference spectra 65 represents known values for a set of color measurements taken from a set of color patches (e.g., 24 color patches for purposes of this example). The same color samples are measured by a color sensing device which is desired to be corrected or calibrated. The measured spectra 80 obtained by the color sensing device is referred to as a "training set". The difference between the measured spectra 80 and the reference spectra 65 is represented by a difference spectra 60. If the difference spectra 60 can be represented by 24 or fewer (the number of color patch measurements made in this example) components 96, then a unique correlation 102 between the measurement error 60 and the original measured spectra 80 can be solved for by using standard algebraic methods (also described in detail below). Components 96 represent a weighted sum of basis components 95 and provides an approximated difference spectra (correction vectors) 61. This correlation 102 describes the relationship between the original measurement and any crosstalk error that it might contain based on the correction vectors 61. This correlation can be used to generate crosstalk correlation factors 103.

Figure 5:
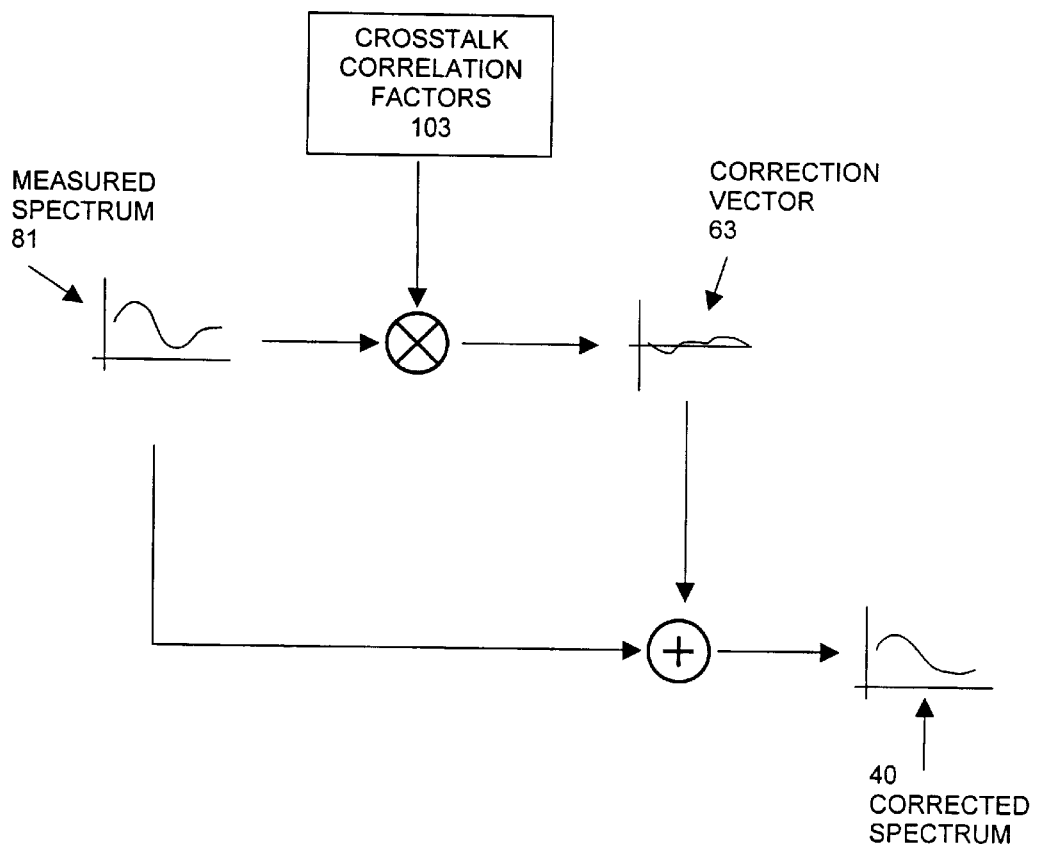
FIG. 5 shows a block diagram representation of the formation of the corrected spectrum for a measured spectrum utilizing the crosstalk correlation factors.

As shown in FIG. 5, once the crosstalk correlation factors are obtained using the training set as discussed in connection with FIG. 4, the crosstalk correlation factors 103 can then be used to correct a color measurement of an unknown color sample made by the color sensing device. The measured spectrum 81 of the unknown color sample can be corrected by multiplying it by the crosstalk correlation factors 103 to provide correction vector 63 for the measured spectrum 81. The correction vector 63 can be added to the original measured spectrum 81 to obtain a new corrected spectrum 40 that no longer contains this crosstalk error.

Figure 6:
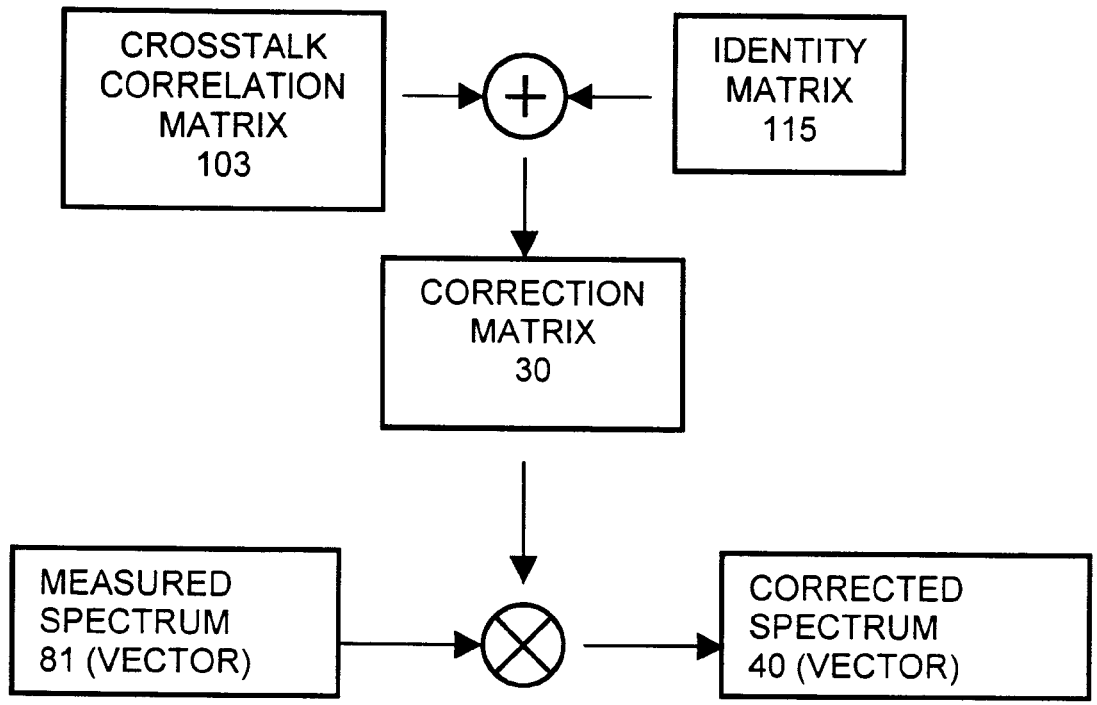
FIG. 6 shows a further block diagram representation of the formation of the corrected spectrum utilizing the crosstalk correlation factors.

FIG. 6 shows that the multiple steps of calculating an error spectrum (i.e. correction vector 63 of FIG. 5) and then adding it to the measurement as discussed in connection with FIG. 5 can be combined into a single matrix multiply operation. The matrix that is used for this one-step procedure is the combination of the crosstalk correlation matrix 103 with an Identity matrix 115. The resulting correction matrix 30 contains the information that correlates the crosstalk error with the spectral measurement 81 which is to be corrected. The actual crosstalk correction amplitudes are obtained by multiplying the measured spectrum 81 by the crosstalk correlation factors 103. As discussed above, once the correction vector (e.g., correction vector 63 of FIG. 5) is obtained, it is added to the measured spectrum 81. Multiplying the measured spectrum 81 by the correction matrix 30 generates, in a single step, a corrected spectrum 40. This is a very general and powerful technique for correcting signals and a number of useful variations are commonly used. Its effectiveness depends critically on the contents of the matrix. The calculation of the matrix elements is described in detail below.

The foregoing discussion has been limited to the correction of crosstalk errors. However, those skilled in the art will appreciate that the methods and apparatus provided by the invention are not so limited, and may be used to correct for various types of error in the measured spectra. The discussion below applies to the correction of any type of error in the measured spectra, including those caused by crosstalk.

Figure 7:
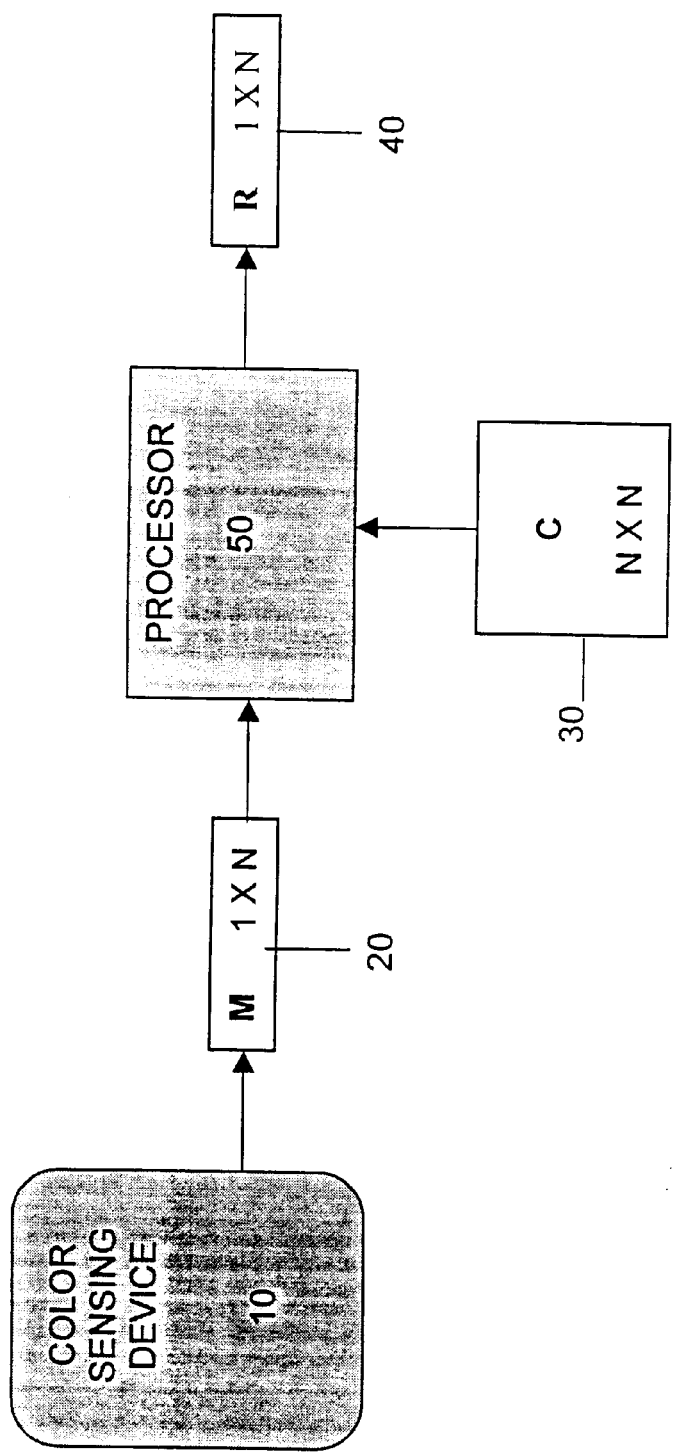
FIG. 7 is a block diagram of an exemplary embodiment of the invention.

In an exemplary embodiment of the invention as shown in FIG. 7, spectral measurements provided by color sensing device 10 (the target instrument) may be corrected. Spectral measurements 20 may be obtained by color sensing device 10. Each of spectral measurements 20 represents an amplitude of detected light in a spectral band from a plurality of respective spectral bands (designated herein as N respective spectral bands). Spectral measurements 20 may be represented by a 1×N spectral measurement vector M, where N refers to the number of measured spectral bands. N×N transform matrix 30 (also referred to herein as correction matrix C) provides mapping between the spectral measurements 20 and corrected spectra. By multiplying 1×N spectral measurement vector M by N×N transform matrix 30, a corrected spectrum 40 may be generated. Corrected spectrum 40 may be represented by 1×N vector R, where R=MC.

Processor 50 (comprising, for example, a conventional microprocessor with suitable software) may be provided for multiplying 1×N spectral measurement vector M by N×N transform matrix C (30) to generate the corrected spectrum R.

N×N transform matrix C (30) may be obtained by calculating a set of basis function weighting vectors based on the difference between measured spectra values for a plurality of color samples and a set of reference spectra values for said color samples.

Figure 8:
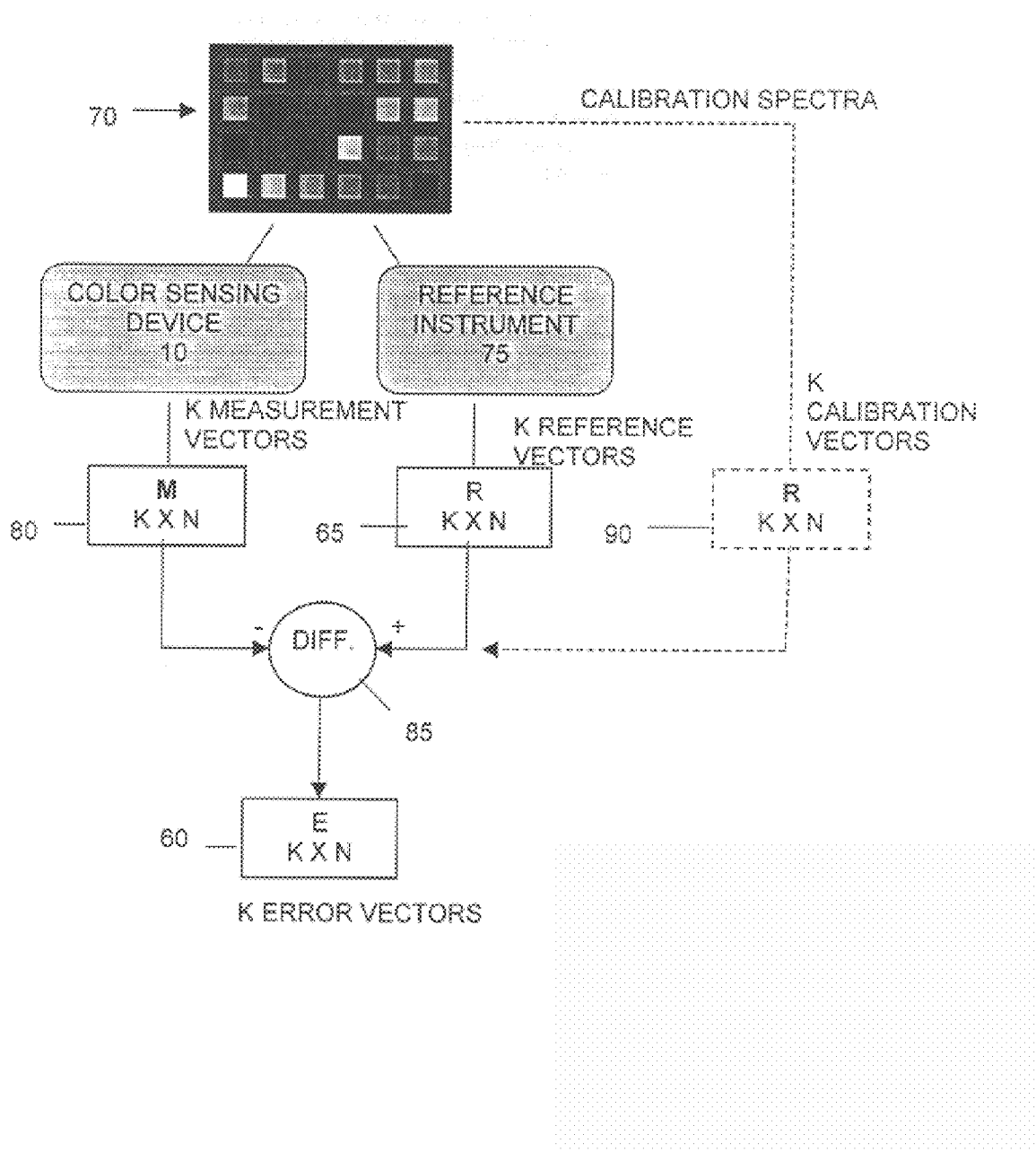
FIG. 8 is a block diagram example of the formation of a set of error vectors for use in forming a set of basis function weighting vectors.

FIG. 8 shows the formation of the spectral difference vectors E (60). Reference spectra values 65 may be obtained from a reference instrument 75. The reference spectra values can be represented by a K×N array of vectors R. Color sensing instrument 10 obtains measurements of a training set of K color samples 70, which measurements are represented by a K×N array of vectors M comprised of K measurement vectors (80). Spectral difference vectors E are obtained by subtracting measured spectra values M from known reference spectra values R (85). As shown in FIG. 8, the same procedure can alternately be used to obtain the spectral difference vector E where calibration values (90) for the K color samples are known. In this instance, measured spectra values M are subtracted from calibration values 90 to obtain the spectral difference vector 60.

Figure 9:
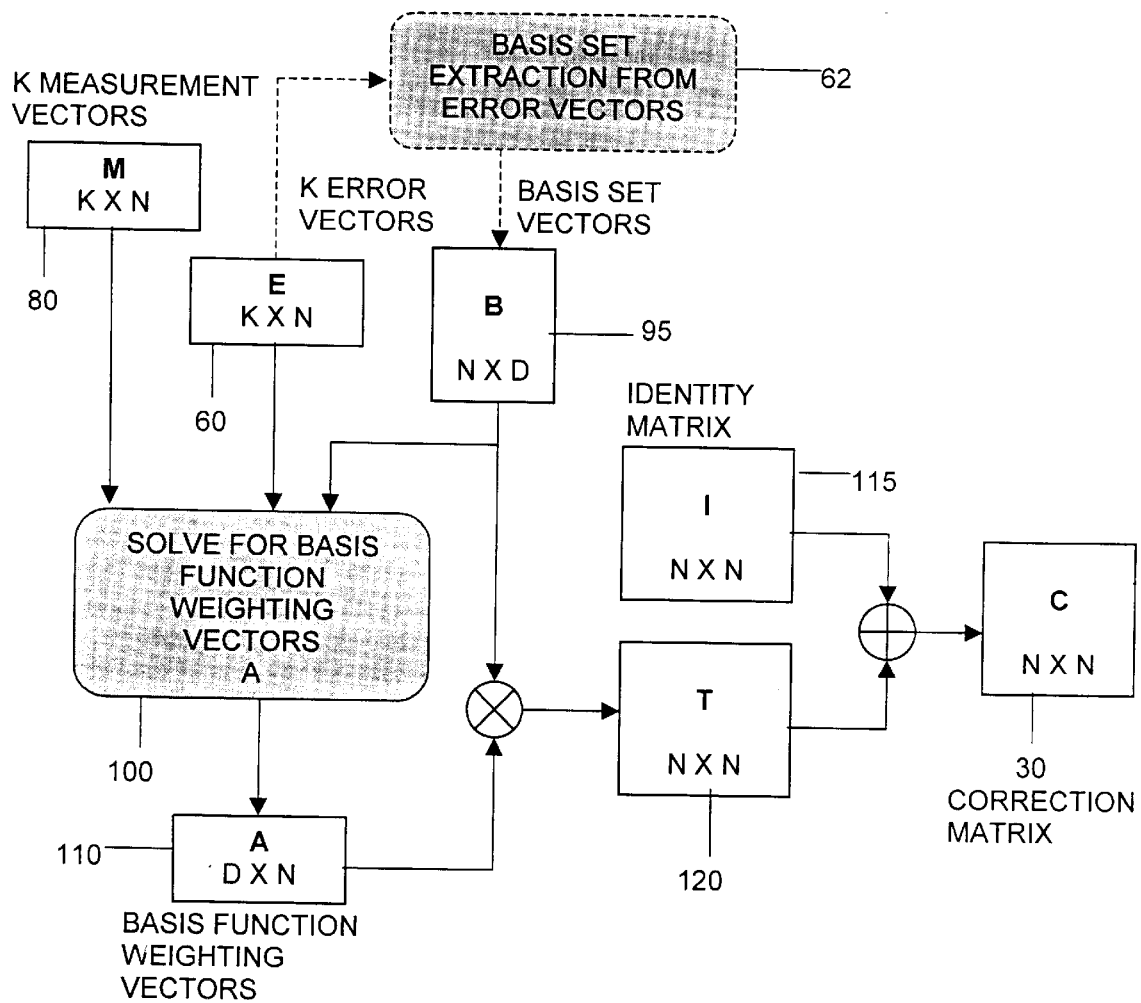
FIG. 9 is a block diagram example of the formation of the correction matrix.

FIG. 9 shows an example of the formation of the N×N transform (correction) matrix 30. As discussed in connection with FIG. 8, each sample K from the training set 70 has a known reference reflectance spectra value. The number of K color samples in the training set (70 of FIG. 8) is less than N. The spectral difference vectors E (60) are obtained as described in connection with FIG. 8. Once the measured spectra vales 80 are obtained by the color sensing device 10, a representation of the difference between the measured spectra values 80 and the reference reflectance spectra values (spectral difference vectors 60) is solved for using a set of D basis functions 95. The number of basis functions (D) may be less than or equal to the lesser of K or N and the basis functions 95 may be represented by the D columns in an N×D array. The solution obtained from the solving step (100) may be designated by an array of D×N amplitudes (basis function weighting vectors 110). The N×N matrix 30 (correction matrix) can then be formed by adding an identity matrix I (115) to the product of the N×D basis set and the D×N amplitude array (120) (referred to above as "crosstalk correlation factors"). The correction matrix 30 can then be used as discussed in connection with FIG. 7 to provide correction for color measurements of an unknown sample made by the color sensing device.

Weightings of basis functions 95 may be stored in color sensing device 10 when basis functions 95 are known and fixed. When basis functions 95 are variable, both basis functions 95 and associated basis function weightings may be stored in color sensing device 10. Basis functions 95 may depend upon characteristics of the differences between the measured spectra values and reference spectra values (60). For example, FIG. 9 shows basis functions 95 as being extracted (62) from the set of error vectors E (60).

In an alternate embodiment, basis functions 95 may comprise principal components of the difference between the measured spectra values and the reference spectra values (e.g., principal components of spectral difference vector E (60)). In such an embodiment, the principal components may be stored in color sensing device 10. The principal components of a system are the functions that represent the highest variances found. The principal components may be selected by forming a covariance matrix of the difference between measured spectra values and reference reflectance spectra values (60 of FIG. 8). The covariance matrix may then be decomposed into a set of orthogonal eigenvectors. The row vectors of the eigenvectors are then normalized to form basis vectors. These basis vectors are then sorted by the magnitude of the corresponding eigenvector. Selecting the first D of the largest vectors from the basis vectors provides the principal components.

A shown in FIG. 8, the known reference reflectance spectra values may be either calibration spectra values 90 or simulation spectra values 65. The known reference reflectance spectra values may be obtained from reference instrument 75.

As discussed above, the present invention provides methods and apparatus for transforming, with minimum error, a spectral color measurement obtained by a target instrument, to the spectrum which would have been obtained by another, reference, instrument. This is accomplished via a linear algebra implementation, using vectors and matrices. A spectrum is represented by a row vector of N spectral samples, each representing the energy in its corresponding spectral band. In the following exemplary description of the invention, it is assumed that the number N is the same for both the target and the reference instrument. This invention does not pertain to changing the number of bands in a spectrum, but when there is a difference between spectra from different instruments, it is common to convert between them using well-established methods of interpolation or averaging.

The following is a detailed explanation of a linear algebra solution which can be used to implement the invention.

The conversion from a target measurement to a reference spectrum is called correction. The correction is accomplished by the vector equation:

$$R = MC$$

Where R is the 1×N reference spectrum, M is the 1×N measured spectrum, and C is the N×N spectral correction matrix. The content of C embodies the (linear) transform between the two instruments (target instrument and reference instrument). C may obtained by processing a set of reference spectra and measured spectra of a number of color specimens having varied spectral characteristics. Because C has dimension N, it takes N linearly independent measurements to completely specify and solve for it. When N is large, as in the case of high resolution spectra, this becomes impractical. Further, it is often the case that the dimensionality of the system is less than the number of samples used to represent a spectrum. When this occurs, solving for C will become difficult or impossible. Even when a solution can be found, it will be unduly sensitive to noise in the measurements, and artifacts in the corrected spectrum will result.

To avoid this condition, yet permit the processing of long spectral vectors, the system is reduced to one with a smaller dimension, D. This smaller system is solved, and the solution used to build the full-size matrix C. To understand the procedure for doing this, first consider the difference between a measured spectrum and a reference spectrum:

$$E=R-M$$

Where E, R, and M are 1×N row vectors representing the error, reference, and measured spectra respectively. E can be represented in terms of the measured spectrum, M by some combination of its N elements:

$$E=MT$$

Where T is some (to be determined) N×N matrix. T represents the mapping from a measurement vector M to its difference from the reference vector R.

The columns of T can be represented by a superposition of basis functions. The number and choice of functions for this purpose will depend on the nature of the difference spectra and the accuracy to which they will be approximated. Trigonometric functions are often used as bases, and the well-known Fourier series results. Other functions are also suitable and may better approximate the underlying physical causes for the differences between the target and reference instruments. A method for obtaining principal components to be used as basis functions is one aspect of this invention.

Whatever their exact form, the basis functions can be evaluated at each of the N spectral bands. Each basis function forms a column in an N×D array, B, where D is the number of basis functions used. These columns, added together with appropriate weighting factors, A, generate the columns of T. Because T is formed from D basis functions, it has dimensionality no larger than D, which can be significantly smaller than N. Further, the basis functions can be selected for properties such as smoothness, which will maintain continuous smooth behavior in the resulting spectrum. Therefore:

$$T=BA$$

$$E \cong MT=MBA$$

If the weighting factors A can be determined, an approximation to the error spectrum can be calculated. The general correction to convert any measurement to a reference spectrum will then be:

$$R=M+E=M+MT=M\ (I+T)=MC$$

Where I is the N×N identity matrix.

The weighting factors A, which result in a good estimate for the difference spectrum, must be determined. There are D rows in A, representing the reduced dimensionality of the system. To solve this smaller system, measurements and reference spectra are obtained for some number K, K>=D, of independent color specimens. The differences between the measurement and reference spectra can then be calculated:

$$E=R-M$$

Where E, R, and M are arrays of K row vectors representing the error, reference, and measured spectra respectively.

The values for the D×N weighting factors which results in the best approximation (in the least-squared-error sense) to the K difference vectors is:

$$A=((MB)^T\ (MB))^{-1}(MB)^T\ E$$

The K color specimens, regarded as the training (reference) set, should be selected with some care. They should be selected to represent a large range of possible spectra that will be encountered. The color specimens in the training set should be spectrally independent of each other, i.e. there should not be duplicate hues, and they should not all be made from combinations of only a few pigments or colorants.

It is also beneficial to have K be >=2D. This reduces the chance that the weights in A are "tuned" to a small set of spectra. By keeping K>2D, the approximation error for the training set is increased slightly, but the error for all spectra outside of the training set is significantly reduced.

The weights determined for A depend on the choice of basis functions. While trigonometric bases, and collections of Gaussian waveforms are effective at representing the difference spectra, their exact specification are empirically determined, and may not be optimal in representing the entire variety of spectral differences in E. As discussed above, the basis functions may comprise principal components, which are very efficient for this purpose. The vector equations for obtaining the principal components of the difference between the measured spectra values and the reference spectra values are described below. The covariance matrix of E is formed:

$$C_V=E^T E$$

The covariance matrix can, by linear algebra methods, be decomposed into a set of orthogonal eigenvectors, U:

$$C_V=U^T \Lambda U$$

where $\Lambda$ is a diagonal matrix of eigenvalues. The row vectors of U, $U_i$ can be normalized to form suitable basis functions for the system:

$$B_i=U_i/(U_i^T U_i)^{-1/2}$$

These basis vectors can be sorted by the magnitude of their corresponding eigenvector. The vector corresponding to the largest eigenvalue represents the largest component of the difference vectors found in E. By selecting the first D vectors from this sorted list, we obtain the best basis set having D components, that can represent E. These are the first D principal components.

It should now be appreciated that the present invention provides advantageous methods and apparatus for transforming, with minimum error, a spectral color measurement obtained by a target instrument, to the spectrum which would have been obtained by another, reference, instrument.

Although the invention has been described in connection with various illustrated embodiments, numerous modifications and adaptations may be made thereto without departing from the spirit and scope of the invention as set forth in the claims.

What is claimed is:

1. A method for correcting spectral measurements of a color sensing device, comprising:

obtaining a set of spectral measurements, each of said measurements representing an amplitude of detected light in a spectral band from a plurality of respective N spectral bands, such that the set of spectral measurements is represented by a 1×N spectral measurement vector;

calculating a set of basis function weighting vectors based on the difference between measured spectra values for a plurality of color samples and a set of reference spectra values for said color samples; and forming an N×N transform matrix based on said basis function weighting vectors and said measured spectra values, said N×N transform matrix providing mapping between the spectral measurements and a corrected spectra; and multiplying the 1×N spectral measurement vector by the N×N transform matrix to generate a corrected spectrum.

2. A method in accordance with claim 1, wherein the set of reference spectra values is obtained from a reference instrument.

3. A method in accordance with claim 1, comprising:

measuring spectra values of K color samples, each sample having a known reference reflectance spectra value;

solving for the basis function weighting vectors based on the difference between measured spectra values and the reference reflectance spectra values using a set of D basis functions, where D is less than or equal to the lesser of K or N and the basis functions are represented by D columns in an N×D array;

designating the basis function weighting vectors as an array of D×N amplitudes; and forming the N×N matrix by adding an identity matrix I to the product of the N×D basis set and the D×N amplitude array.

4. A method in accordance with claim 3, comprising:

storing weightings of the basis functions in the color sensing device when the basis functions are known and fixed.

5. A method in accordance with claim 3, comprising:

storing the basis functions and associated basis function weightings in the color sensing device when the basis functions are variable.

6. A method in accordance with claim 3, wherein the basis functions depend upon characteristics of the differences between the measured spectra values and the reference spectra values.

7. A method in accordance with claim 3, wherein the basis functions comprise principal components of the difference between the measured spectra values and the reference spectra values.

8. A method in accordance with claim 7, comprising:

storing the principal components in the color sensing device.

9. A method in accordance with claim 3, wherein the known reference reflectance spectra values are one of calibration spectra or simulation spectra.

10. A method in accordance with claim 3, wherein the known reference reflectance spectra values are obtained from a reference instrument.

11. Apparatus for correcting spectral measurements of a color sensing device, said color sensing device obtaining a set of spectral measurements, each measurement representing an amplitude of detected light in a spectral band from a plurality of respective N spectral bands, such that the set of spectral measurements is represented by a 1×N spectral measurement vector, said apparatus comprising:

an N×N transform matrix that provides mapping between the spectral measurements and corrected spectra; and a processor for multiplying the 1×N spectral measurement vector by the N×N transform matrix to generate a corrected spectrum;

wherein said N×N transform matrix is obtained by:

calculating a set of basis function weighting vectors based on the difference between measured values for a plurality of color samples and a set of reference spectra values for said color samples; and forming said N×N transform matrix based on said basis function weighting vectors.

12. Apparatus in accordance with claim 11, further comprising a reference instrument for obtaining the set of reference spectra values.

13. Apparatus in accordance with claim 11, wherein the N×N transform matrix is obtained by:

measuring spectra values of K color samples at the color sensing device, each sample having a known reference reflectance spectra value;

solving for a the basis function weighting vectors based on the difference between measured spectra values and the reference reflectance spectra values at the processor using a set of D basis functions, where D is less than or equal to the lesser of K or N and the basis functions are represented by D columns in an N×D array;

designating at the processor the basis function weighting vectors as an array of D×N amplitudes; and forming at the processor the N×N matrix by adding an identity matrix I to the product of the N×D basis set and the D×N amplitude array.

14. Apparatus in accordance with claim 13, wherein:

weightings of the basis functions are stored in the color sensing device when the basis functions are known and fixed.

15. Apparatus in accordance with claim 13, wherein:

the basis functions and associated basis function weightings are stored in the color sensing device when the basis functions are variable.

16. Apparatus in accordance with claim 13, wherein the basis functions depend upon characteristics of the differences between the measured spectra values and the reference spectra values.

17. Apparatus in accordance with claim 13, wherein the basis functions comprise principal components of the difference between the measured spectra values and the reference spectra values.

18. Apparatus in accordance with claim 17, wherein:

the principal components are stored in the color sensing device.

19. Apparatus in accordance with claim 13, wherein the known reference reflectance spectra values are one of calibration spectra or simulation spectra.

20. Apparatus in accordance with claim 13, wherein the known reference reflectance spectra values are obtained from a reference instrument.

21. A method for correcting spectral measurements of a color sensing device, comprising:

obtaining a set of spectral measurements, each of said measurements representing an amplitude of detected light in a spectral band from a plurality of respective N spectral bands, such that the set of spectral measurements is represented by a 1×N spectral measurement vector;

measuring spectra values of K color samples, each sample having a known reference reflectance spectra;

solving for a set of basis function weighting vectors based on the difference between measured spectra values and the reference reflectance spectra values using a set of D basis functions, where D is less than or equal to the lesser of K or N and the basis functions are represented by D columns in an N×D array;

designating the basis function weighting vectors as an array of D×N amplitudes; and forming an N×N transform matrix by adding an identity matrix I to the product of the N×D basis set and the D×N amplitude array; and multiplying the 1×N spectral measurement vector by the N×N transform matrix to generate a corrected spectrum.

22. Apparatus for correcting spectral measurements of a color sensing device, said color sensing device obtaining a set of spectral measurements, each measurement representing an amplitude of detected light in a spectral band from a plurality of respective N spectral bands, such that the set of spectral measurements is represented by a 1×N spectral measurement vector, said apparatus comprising:

an N×N transform matrix that provides mapping between the spectral measurements and corrected spectra; and a processor for multiplying the 1×N spectral measurement vector by the N×N transform matrix to generate a corrected spectrum;

wherein the N×N transform matrix is obtained by:

measuring spectra values of K color samples at the color sensing device, each sample having a known reference reflectance spectra value;

solving for a set of basis function weighting vectors based on the difference between measured spectra values and the reference reflectance spectra values at the processor using a set of D basis functions, where D is less than or equal to the lesser of K or N and the basis functions are represented by D columns in an N×D array;

designating at the processor the basis function weighting vectors as an array of D×N amplitudes; and forming at the processor the N×N matrix by adding an identity matrix I to the product of the N×D basis set and the D×N amplitude array.

* * * * *